(12) United States Patent
Palma et al.

(10) Patent No.: US 8,335,809 B2
(45) Date of Patent: Dec. 18, 2012

(54) PROCEDURE FOR DERIVING A THREE-DIMENSIONAL DIGITAL MASK STARTING FROM A SERIES OF TWO-DIMENSIONAL MASKS, PLUS A DEVICE FOR DOING THIS

(75) Inventors: Giovanni Palma, Le Kremlin Bicetre (FR); Serge Muller, Guyancourt (FR); Razvan Iordache, Paris (FR)

(73) Assignee: General Electric Company, Schenectady, NY (US)

( * ) Notice: Subject to any disclaimer, the term of this patent is extended or adjusted under 35 U.S.C. 154(b) by 1033 days.

(21) Appl. No.: 12/339,209

(22) Filed: Dec. 19, 2008

(65) Prior Publication Data

US 2009/0164541 A1    Jun. 25, 2009

(30) Foreign Application Priority Data

Dec. 20, 2007    (FR) ..................................... 07 60151

(51) Int. Cl.
*G06F 17/17*    (2006.01)
*G06K 9/00*    (2006.01)

(52) U.S. Cl. ........ 708/201; 708/291; 382/128; 382/131; 382/132

(58) Field of Classification Search .................. 708/290, 708/291; 382/128, 131, 132
See application file for complete search history.

(56) References Cited

U.S. PATENT DOCUMENTS

| | | | |
|---|---|---|---|
| 7,231,077 B2* | 6/2007 | Eck et al. ....................... | 382/132 |
| 7,386,158 B2* | 6/2008 | Yamada ......................... | 382/132 |
| 8,098,920 B2* | 1/2012 | Palma et al. .................. | 382/132 |
| 2005/0089205 A1* | 4/2005 | Kapur et al. ................... | 382/128 |
| 2007/0036418 A1* | 2/2007 | Pan et al. ...................... | 382/131 |

* cited by examiner

*Primary Examiner* — Tammara Peyton
(74) *Attorney, Agent, or Firm* — Global Patent Operation

(57) ABSTRACT

A derivation procedure for a three-dimensional digital mask from a series of two-dimensional masks in a radiographic device containing a source (S) of X-rays, a means of recording and a volume of interest hat contains the object to be X-rayed located between the source (S) and the means of recording consists of an extrapolation of each mask $M_{\theta 2}$ includes determining a last segment $1_{fin}$ beyond the limits of the means of recording; and working out a two-dimensional mask $M_\gamma$ associated with a position $S_\gamma$ of the source, for any angle γ included in the angular range $\theta_2$ to $\theta_1$ (a position close to $\theta_2$). For every parallel segment 1 located between segment d (or d' respectively) and segment $1_{fin}$, the procedure further includes deriving a three-dimensional mask (21) of the object for each voxel at the intersection of plane $P_1^{\theta 2}$ and the volume of interest; and projecting the three-dimensional mask onto the segment 1.

14 Claims, 5 Drawing Sheets

PROCEDURE FOR DERIVING A THREE-DIMENSIONAL DIGITAL MASK STARTING FROM A SERIES OF TWO-DIMENSIONAL MASKS, PLUS A DEVICE FOR DOING THIS

CROSS-REFERENCE TO RELATED APPLICATIONS

This application claims priority under 35 U.S.C. §119(a)-(d) or (f) to prior-filed, co-pending French patent application serial number 0760151, filed on Dec. 20, 2007, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

The field of the invention relates to radiographic devices and methods generally. More particularly, the field of the invention is concerned with an extrapolation procedure for a two-dimensional mask and a procedure for working out a three-dimensional mask based on an extrapolated series of two-dimensional masks, these procedures being intended for use in a radiographic device, particularly of the tomosynthesis type.

2. Description of Related Art

In any tomosynthesis application, it can be interesting to be able to extrapolate a two-dimensional mask for an object projected at the level of truncated views of the object, and then to be able to estimate a three-dimensional mask based on a series of two-dimensional masks extrapolated in this way. This extrapolation of the two-dimensional masks is indeed useful when it is necessary to have an estimate of the signal outside the physical limits of the detector during reconstruction. The three-dimensional mask can be used as a priori information in iterative reconstruction methods in order to speed up the reconstruction while focusing only on the voxels that belong to the object under consideration, or in order to eliminate artefacts that the reconstruction has created outside the object under consideration. The principle difficulties in constructing reliable three-dimensional masks derive from the limited angular interval swept out by the source and the truncation of the object under consideration in some projections as a result of the finite dimensions of the detector.

For example, in the case of digital tomosynthesis of the breast, such tomosynthesis is a new imaging technique for the breast using three-dimensional tomography that is restricted in terms of angles. It allows the problem of superposition in the detection of lesions to be largely circumvented. Multiple views projected from different angles of acquisition potentially reduce the number of false positives due to the addition of artefacts, and the number of false negatives due to masking effects by the covering tissues. During the tomosynthesis examination, a series of images is obtained for a variety of angles of acquisition with the aim of reconstructing a three-dimensional representation of the breast. During the reconstruction procedure, knowing for a given voxel v of the three-dimensional representation whether or not it has information about the breast can help reduce the artefacts as well as the calculation time. This knowledge can be represented with the help of a three-dimensional mask M of the breast: $M[v]=1$ if v belongs to the breast and $M[v]=0$ otherwise. As this mask M has been reconstructed using the two-dimensional masks deriving from the series of images acquired earlier, the assumption is made that all the voxels of the region of interest are located within the limits of the detector. However, in reality there are voxels in the region of interest that are not projected within the limits of the detector when certain images within the series are being acquired. This means that the two-dimensional mask for the breast outside the limits of the detector has to be estimated. Without a priori information, the natural approach is to decide that all pixels outside the limits of the detector are part of the breast. This way, the two-dimensional masks (and consequently the three-dimensional ones) never underestimate the shape of the breast, because they are always larger than that shape. As a result, when the three-dimensional mask is constructed, artefacts can appear: staircases. The contour of the resulting mask is therefore a poor estimation of what it really should be, and the shape of the mask is not continuous. In consequence, using the three-dimensional mask obtained this way on the three-dimensional representation produces an unnatural skin line in the final three-dimensional representation, which complicates the diagnoses that the practitioners make based on it.

BRIEF SUMMARY OF THE INVENTION

One aim of an embodiment of the invention is to provide an extrapolation procedure for two-dimensional masks of an object in views with truncated projections (in order that the mask extrapolated using a specific projection will be regular and consistent with the two-dimensional masks made using other projections) and to reconstruct a three-dimensional mask of the object acquired that does not underestimate the object and which is regular, in the sense that the truncation of the views does not introduce any discontinuities in the mask.

To achieve this, the exemplary embodiment of the invention envisages an extrapolation procedure for a two-dimensional mask $M_{\theta 2}$ in a radiographic device of the type containing a mobile X-ray source taking up at least two positions $S_{\theta 1}$ and $S_{\theta 2}$ in space, associated with their respective two-dimensional masks $M_{\theta 1}$ and $M_{\theta 2}$, a means of recording that is in an essentially planar arrangement opposite the source and which contains a limit (d, d') and a volume of interest consisting of an object that is suitable for radiography, located between the source and the means of recording, the procedure consisting of the following steps:

a) at least partial estimation of a series of two-dimensional masks $M_\gamma$ associated with a series of positions $S_\gamma$ for the source, located between the source's positions $S_{\theta 1}$ and $S_{\theta 2}$, starting from the two-dimensional masks $M_{\theta 1}$ and $M_{\theta 2}$ b) at least partial evaluation of an intermediate three-dimensional mask for the object, starting from the series of two-dimensional masks $M_\gamma$ and the two-dimensional masks $M_{\theta 1}$ and $M_{\theta 2}$ c) extrapolation of the two-dimensional mask $M_{\theta 2}$ beyond the limits d or d' of the means of recording, according to a relative position between $S_{\theta 1}$ and $S_{\theta 2}$, starting from the intermediate three-dimensional mask A beneficial but optional part of the procedure in accordance with the invention includes at least one of the following features:

before step a), if the two-dimensional mask $M_{\theta 1}$ associated with the source position $S_{\theta 1}$ is not available, the two-dimensional mask $M_{\theta 1}$ is extrapolated from the available two-dimensional masks $M_\theta$;

the extrapolation of step c) involves projection of the intermediate three-dimensional mask based on position $S_{\theta 2}$ onto a plane passing through the means of recording;

the (at least partial) working out from step a) is carried out at the limit d or d' of the means of recording, according to the relative position between $_{\theta 1}$ and $S_{\theta 2}$;

for each of the two-dimensional masks $M_\gamma$, the (at least partial) estimation from step a) involves a step that determines a point $T_\gamma$ situated at an edge of the object, projected onto the limit d or d' of the means of recording, with the source at position $S_\gamma$ the points $T_\gamma$ are estimated by linear interpolation between the points $T_{\theta 1}$ and $T_{\theta 2}$ located at an edge of the object project onto the limit d or d' of the means of recording (10), with the source (S) at positions $S_{\theta 1}$ and $S_{\theta 2}$ respectively;

if the two-dimensional mask $M_{\theta 1}$ associated with source position $S_{\theta 1}$ is not available, point $T_{\theta 1}$ is then extrapolated from the points $T_\theta$ that are available;

the procedure includes a supplementary step of:

d) applying a closure function to the extrapolated two-dimensional mask $M_{\theta 2}$;

before step a), the procedure involves a step for determining a limit of extrapolation $l_{fin}$, that is effectively parallel to the limit d or d' of the means of recording and that is located outside the limits of the means of recording;

for every line l that is that is effectively parallel to the limit of extrapolation $l_{fin}$ and located between the limit d or d' of the means of recording and the limit of extrapolation $l_{fin}$, step b) involves the following substeps:

b1) working out a plane $P_1^{\theta 2}$ that passes through position $S_{\theta 2}$ and the line l b2) working out an intermediate three-dimensional mask for each voxel (v) located at the intersection of the plane $P_1^{\theta 2}$ and the volume of interest; and step c) involves a projection step for every line l that is that is effectively parallel to the limit of extrapolation $l_{fin}$, and located between the limit d or d' of the means of recording and the limit of extrapolation $l_{fin}$, for the intermediate three-dimensional mask.[0011] In accordance with the invention, an extrapolation procedure is also envisaged for a series of two-dimensional masks $M_\theta$ in a radiographic device, with the feature that each two-dimensional mask $M_\theta$ in the series of two-dimensional masks is extrapolated by a procedure exhibiting at least one of the features described earlier.

A beneficial but optional part of the procedure in accordance with an embodiment of the invention includes at least one of the following features:

the procedure that employs at least one of the features listed earlier is applied iteratively, and at each iteration, the means of recording are extended into their adjacent virtual equivalents corresponding to a common part of the two-dimensional masks $M_\theta$ already extrapolated.

To achieve this, an embodiment of the invention envisages a calculation procedure for a three-dimensional mask based on a series of two-dimensional masks $M_\theta$ in a radiographic device of the type containing a mobile X-ray source taking up at least two positions $S_{\theta 1}$ and $S_{\theta 2}$ in space, associated with their respective two-dimensional masks $M_{\theta 1}$ and $M_{\theta 2}$, a means of recording that is in an essentially planar arrangement opposite the source and which has a limit d or d' and a volume of interest consisting of an object that is suitable for radiography, located between the source and the means of recording, with the procedure consisting of the following steps:

a) extrapolation of the series of two-dimensional masks $M_\theta$ by a procedure featuring at least one of the previously listed characteristics, and b) determination of a three-dimensional digital mask based on the extrapolated series of two-dimensional masks $M_\theta$.

A beneficial but optional part of the procedure in accordance with an embodiment of the invention includes at least the following features:

step b), comprising the following sub-steps:

b1) application of a dilation function followed by a low-pass filter to obtain a membership function $\mu_{M\theta}$ for each two-dimensional mask $M_\theta$ b2) evaluation of a membership function $\mu_{M3d}$ based on the membership function $\mu_{M3d}$, using a T-norm operator b3) determination of the three-dimensional digital mask based on the membership function $\mu_{M3d}$, and the t-norm operator is a probabilistic one.

In accordance with an embodiment of the invention, a radiographic device is envisaged of the type that has:

a mobile source of X-rays that moves along a circular arc with centre C;

means of recording, in an essentially planar arrangement opposite the source;

a volume of interest, containing an object suitable for radiographic examination, located between the source and the means of recording;

a means of initiating a procedure featuring at least one of the characteristics listed earlier.

Other characteristics and benefits of embodiments of the invention will appear in the course of the description that follows of a mode of realization of the invention plus variants.

BRIEF DESCRIPTION OF THE DRAWINGS

With regard to the drawings attached.

DETAILED DESCRIPTION OF THE INVENTION

Figure 1:
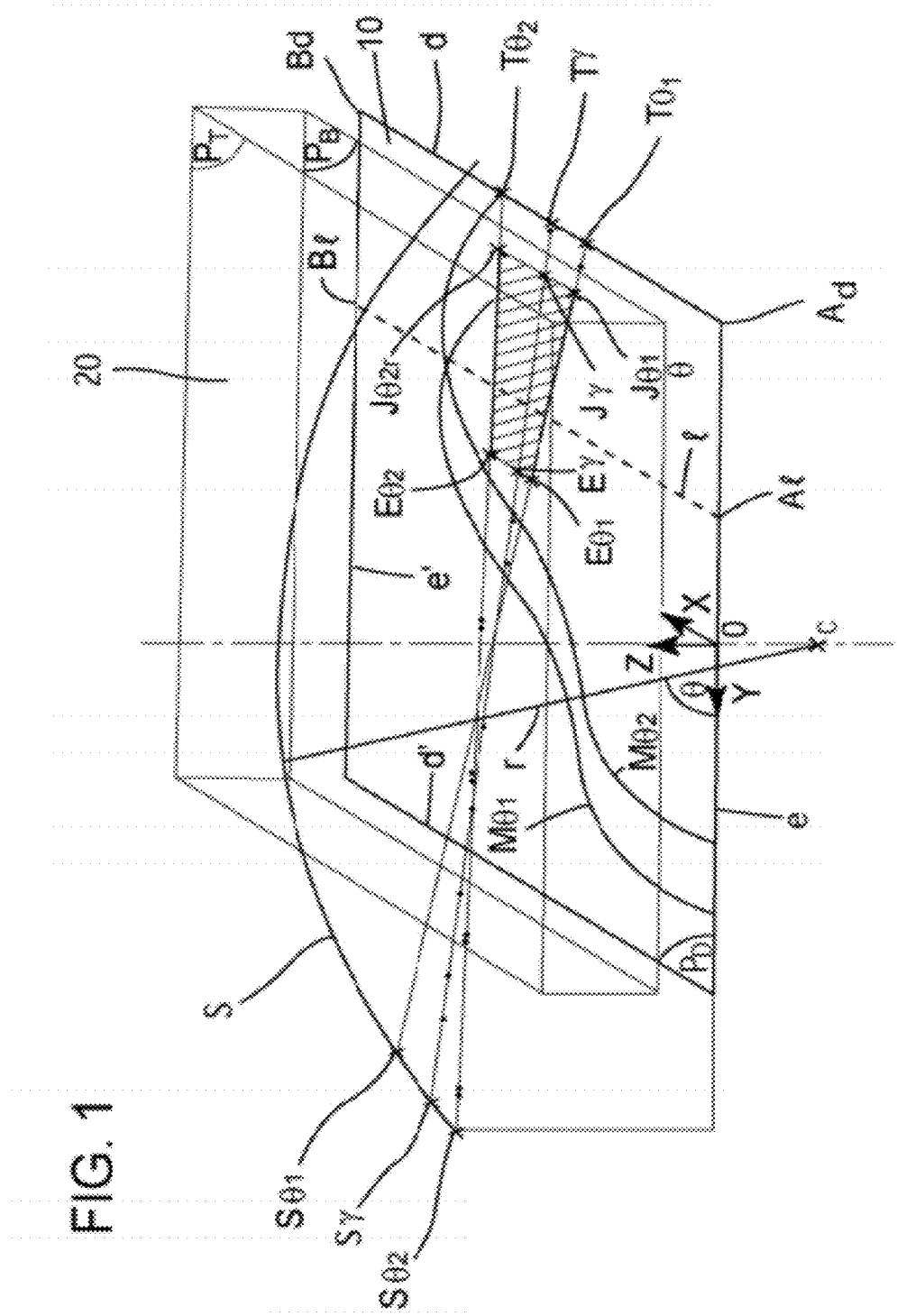
FIG. 1 gives a three-dimensional diagram of a device and of the procedure in accordance with the invention.

With reference to FIG. 1: a radiographic device suitable for producing imagery by three-dimensional tomography contains a means of recording 10 that takes the form of a digital detector that is effectively flat and defines a plane $P_D$. A digital detector such as this comprises a matrix of detectors each of which represents a pixel p, uniformly distributed into lines and columns. The radiographic device also includes an X-ray source opposite the means of recording and which is mobile with respect to this same means of recording. The X-ray source, which will generally be an X-ray generator tube, is suitable for being moved in discrete steps along a trajectory S that is effectively a circle of radius r and centre C. The trajectory S is restricted in terms of angle to an interval of range $[\theta_{min}; \theta_{max}]$, where $0 \leq \theta_{min} < \theta_{max} \leq \pi$, and where the angles are measure with respect to the plane $P_D$ of the detector. At each discrete source position $S_\theta$ along this trajectory S, there are an associated angle $\theta$ in the range $[\theta_{min}; \theta_{max}]$, an image $I_\theta$ projected and captured by the detector 10, and a two-dimensional mask $M_\theta$.

Furthermore, there is a volume of interest 20 situated between the X-ray source and the means of recording 10, suitable for containing an objected intended for X-ray examination by the radiographic device. This region of interest 20 is delimited in part by a bottom plane $P_B$ and a top plane $P_T$. The planes $P_B$ and $P_T$ are effectively parallel to the detection plane $P_D$, defined by the means of recording 10. The volume of interest is furthermore delimited by four planes (not shown) passing through each of the edges d, d', e and e' of the detector and effectively perpendicular to the planes $P_B$ and $P_T$. The region of interest 20 is thus shaped as a parallelepiped rectangle, as illustrated in FIG. 1. In the case of a device for digital tomosynthesis of the breast, the region of interest 20 is delimited by a cushion to support the breast, the upper face of which is in plane $P_B$ and the lower surface lies within plane $P_D$, a compression plate of which the lower face lies in plane $P_T$, such that the planes are basically parallel with the patient's torso and pass through the first at last lines (e and e') of pixels on the detector, and planes effectively perpendicular to the ones just mentioned, passing through the first at last columns (d and d') of pixels on the detector.

The classical method for describing a three-dimensional digital mask $M_{3d}$ for the object situated within the volume of interest 20 is as follows:

$$M3d[v] = \begin{cases} 1 & \text{if } v \text{ is within the object} \\ 0 & \text{otherwise} \end{cases}$$

for all voxels v within the volume of interest 20. A two-dimensional mask $M_\theta$ is thus a projection of this mask $M_{3d}$ corresponding to one position $S_\theta$ of the source, as seen on the plane $P_D$ of the detector 10, and it is defined by:

$$M\theta \begin{cases} 1 & \text{if } p \text{ belongs to the area in which the object is projected} \\ 0 & \text{otherwise} \end{cases}$$

for all pixels p in the plane $P_D$ of the detector.

Let proj: $[0; \pi] \times R^3 \to P_D$ be the application that associates a voxel v of space $R^3$ containing the volume of interest 20 and an angle $\theta$ with the projection onto the plane $P_D$ corresponding to position $S_\theta$ of the source. We then have:

$$\forall p \in P_D, \forall v \text{ such that } p = proj(\theta, v) \; M_{3d}[v] = 1 \Rightarrow M_\theta[p] = 1$$

$$M_\theta[p] = 0 \Rightarrow M_{3d}[v] = 0$$

which means, for a given position S of the source, that all the voxels projected outside a region of the object on plane $P_D$ of the detector do not belong to the three-dimensional digital mask for the object in question.

Notation

A reference frame O used hereafter in the description is described by the plane $P_D$ of the detector and the plane that is perpendicular to it, passing through the first line of pixels e in the detector and which contains the trajectory of the source. An x-axis is therefore aligned with the column d of pixels in the detector and oriented from the first line e towards the last line e'. A y-axis is located along the first line e and oriented from the last column d towards the first column d'. The origin of the reference frame is located in plane $P_D$ such that the centre C of the trajectory of the source has coordinates (0,0, $z_C$).

Within this reference frame, each voxel v of the space $R^3$ has coordinates $(x_v, y_v, z_v)$. [0029] $\forall \theta \in [0; \pi]$, $S_\theta$ is the position of the source on the trajectory of angle $\theta$ with respect to the y-axis. Therefore $\forall \theta \in [0; \pi]$, $x_{S\theta} = 0$; $y_{S\theta} = r \cos(\theta)$, $z_{S\theta} \leq r \sin(\theta) + z_C$.

$y_d$ is the ordinate of the last column d; $y_{d'}$ is that of the first column d'.

$\forall \theta \in [0; \pi]$, $T_\theta$ is the point located on the final column d of the detector (or the first column d' respectively), the point corresponding to an edge of the object situated within the volume of interest 20 in the projection associated with angle $\theta$.

$\forall \theta \in [0; \pi]$ points $E_\theta$ and $J_\theta$ are the intersection points of the line segment $S_\theta T_\theta$ and the planes $P_T$ and $P_B$ respectively.

For a column 1 of pixels in the detector, $A_1 = (x_e = 0, y_1, 0)$ is the point corresponding to the first pixel of the detector in column 1, and $B_1 = (x_{e'}, y_1, 0)$ is the point corresponding to the last pixel of the detector in this column 1. Let $P_1^\theta$ be the plane passing through the three points $S_\theta$, $A_1$ and $B_1$.

Description of a Procedure in Accordance with an Embodiment of the Invention As the points $T_\theta$ are on the edge of the object as projected at the last column d (or the first column d' respectively), the line segments $S_\theta T_\theta$ are tangential to the edge of the object in the three-dimensional digital mask $M_{3d}$. As the volume of interest 20 is delimited by planes $P_T$ and $P_B$, this means that the line segments $E_\theta J_\theta$ are tangential to the said edge of the object. The idea of the procedure in accordance with the invention is to use these segments to define an intermediate three-dimensional mask M~ enveloping the object and to project this intermediate three-dimensional mask outside the limits of the detector as represented by the last column D (and the first column d' respectively) in a manner allowing the two-dimensional masks $M_\theta$ to be extrapolated, one column of pixels at a time.

Let us suppose that we want to extrapolate a two-dimensional mask $M_{\theta 2}$, associated with an angle $\theta_2$ and a specific source location $S_{\theta 2}$ at the position of a column 1 of pixels that is beyond the limits of the detector. We therefore have $y_1 < y_d < 0$ (and $y_1 > y_d > 0$ respectively) within the frame of reference O in FIG. 1. Let us take an angle $\theta_1 > \theta_2$ (or $\theta_1 < \theta_2$ respectively) corresponding to a particular source position $S_{\theta 1}$ close to position $S_{\theta 2}$. So as not to overload this proposition, let us assume that there is only a single point $T_{\theta 2}$ and a single point $T_{\theta 1}$ (the case of several points $T_\theta$ will be treated later on). For all angles $\gamma$ in the interval from $\theta_1$ to $\theta_2$, we work out the position of the point $T_\gamma$ on the final column d (or the first column d' respectively) making use of a linear interpolation between $T_{\theta_1}$ and $T_{\theta_2}$:

$$\begin{cases} x_{T_{\theta_1}} = \alpha\theta_1 + \beta \\ x_{T_{\theta_2}} = \alpha\theta_2 + \beta \\ x_{T_\gamma} = \alpha\gamma + \beta \end{cases}$$

where $\alpha$ and $\beta$ are constants.

This then gives the coordinates of the point $T_\gamma$:

$$T_\gamma = \left(\frac{x_{T_{\theta_2}} - x_{T_{\theta_1}}}{\theta_2 - \theta_1}\gamma + x_{T_{\theta_1}} - \frac{x_{T_{\theta_2}} - x_{T_{\theta_1}}}{\theta_2 - \theta_1}\theta_1, y_d, 0\right)$$

A surface defined by $\{S_\gamma T_\gamma | \gamma \in [\theta_1; \theta_2]\}$ therefore delimits a frontier region of the intermediate three-dimensional mask M~ containing, in the manner worked out above, the object in question.

The extrapolation of the two-dimensional mask $M_{\theta_2}$ onto the column of pixels 1 is done by projecting the intermediate three-dimensional mask M~ onto the plane $P_D$ of the detector 10, taking the source to be located at position $S_{\theta_2}$.

In the case in question, we use a first step to work out the final column d (or the first column d' respectively) in a two-dimensional mask $M_\gamma$ associated with the source position $S_\gamma$ for angle $\gamma$, which is between $\theta_1$ and $\theta_2$:

$$\forall p \in [A_d B_d], M_\gamma[p] = \begin{cases} 1 & \text{if } xp \leq X_{T_\gamma} \\ 0 & \text{otherwise} \end{cases}$$

Figure 2:
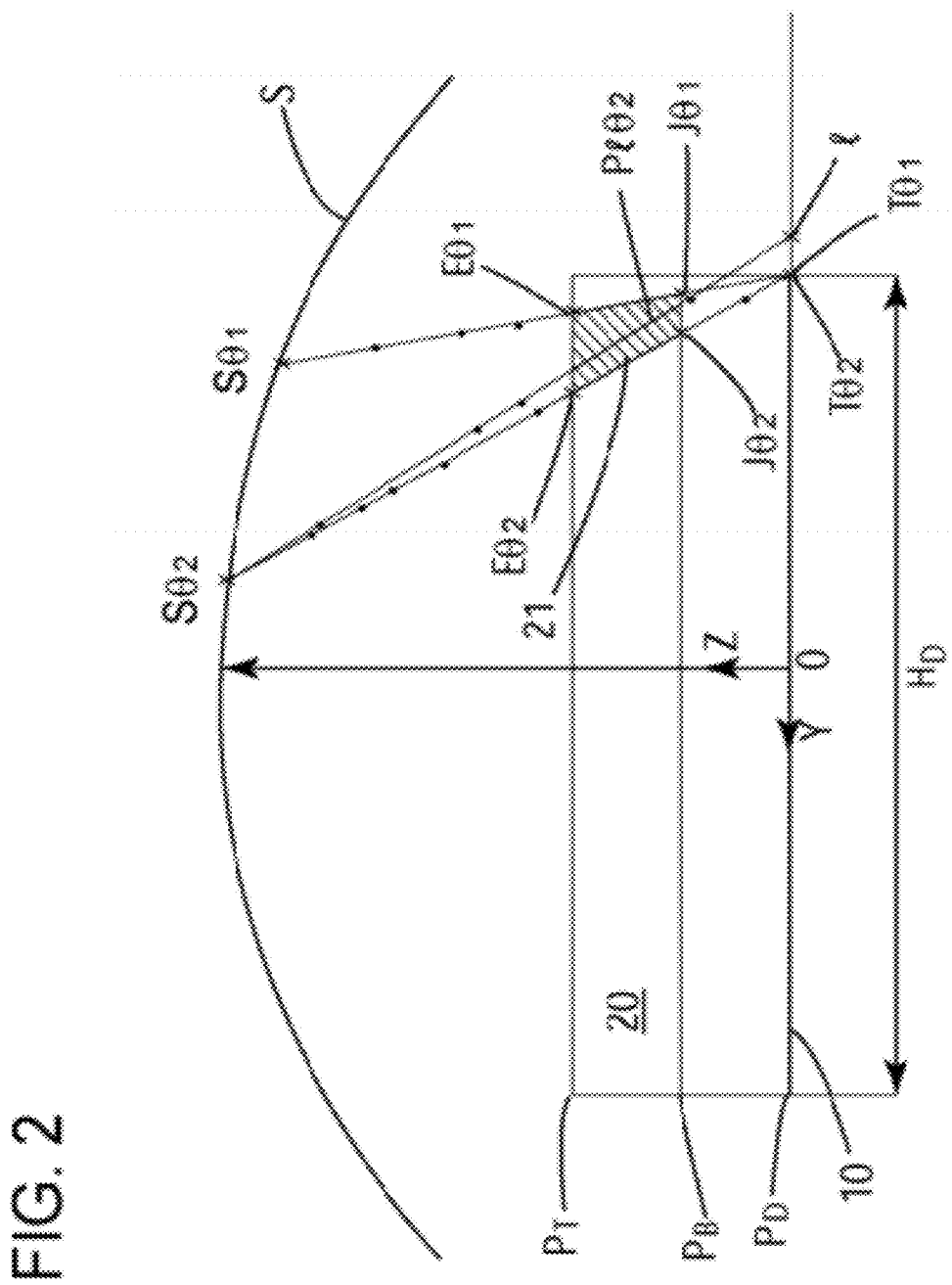
FIG. 2 is a schematic view of the side of the device and of the procedure of FIG. 1 allowing the extrapolation of a two-dimensional mask $M_{\theta 2}$ onto a segment 1.
Figure 3:
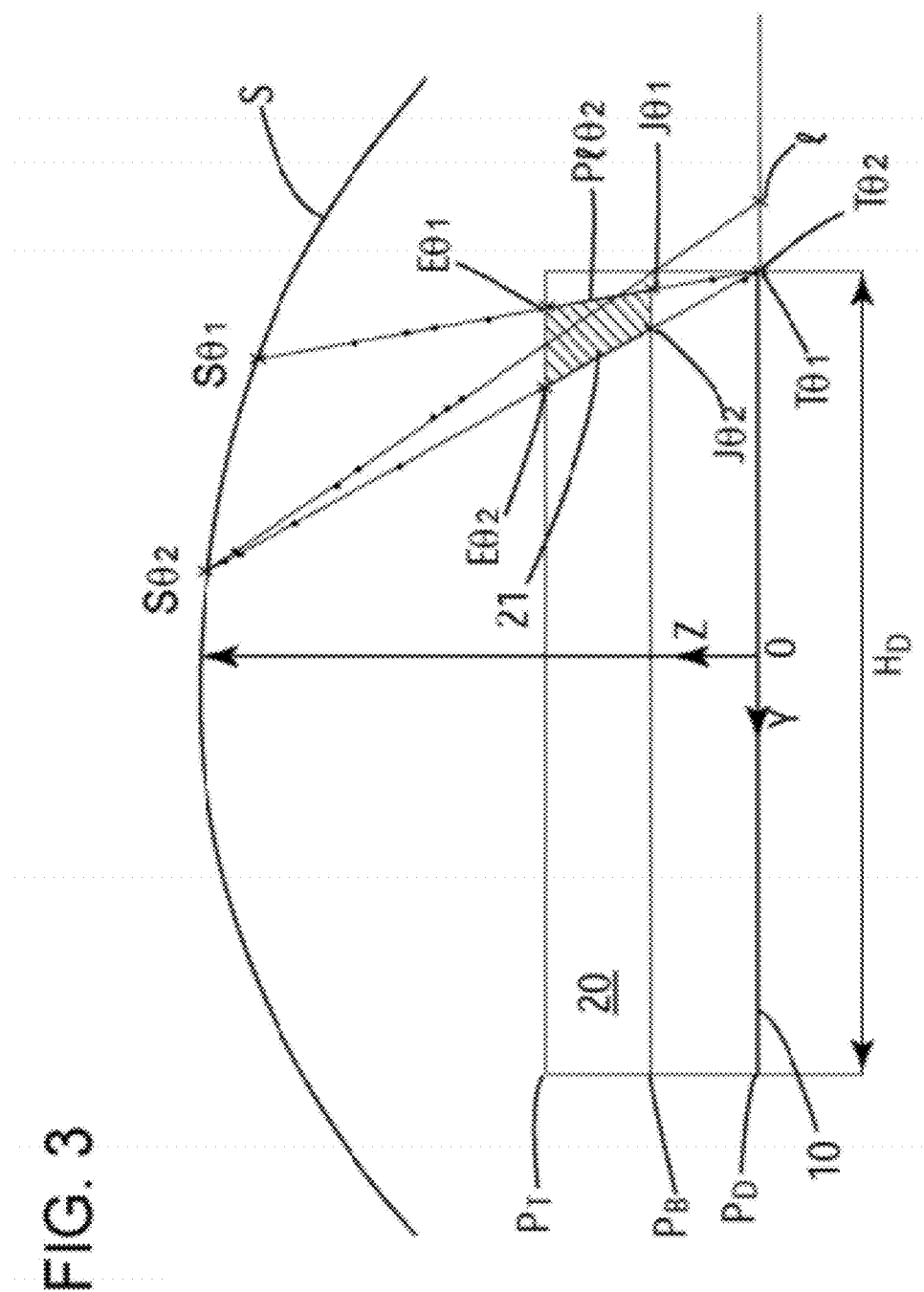
FIG. 3 is a schematic view from the side similar to FIG. 2 but not allowing the extrapolation of the two-dimensional mask $M_{\theta 2}$ onto the segment 1.

In a second step, we work out the intersection between a three-dimensional envelope for the object under consideration and a plane $P_1^{\theta_2} = S_{\theta_2} A_1 B_1$, a plane that therefore contains column 1 or pixels onto which the extrapolation is to be performed for the two-dimensional mask $M_{\theta_2}$. With reference to FIGS. 2 and 3: there is a portion 21 of the volume of interest 20 that is "seen" by the means of recording 10 when the source is in position $S_{\theta_1}$ but not when the source is in position $S_{\theta_2}$. For every voxel v that belongs to the intersection of plane $P_1^{\theta_2}$ and the volume of interest, there is an angle $\gamma$ between $\theta_1$ and $\theta_2$ such that the voxel v is projected onto the final column d (or the first column d' respectively) when the source is in position $S_\gamma$. Point $S_\gamma$ is the intersection between a line passing through $A_d$ (or $A_{d'}$ respectively) and the point (0, $y_v$, $z_v$) and the locus S of the source. A necessary condition at all times is that the angle $\gamma$ exists such that all the voxels v of the intersection between the volume of interest 20 and the plane $P_1^{\theta_2}$ can be projected onto the last column d (or first column d' respectively):

$$y_t > \max(y_{proj(\theta_2, E_{\theta_1})}, y_{proj(\theta_2, J_{\theta_1})})$$

and $$y_t < \min(y_{proj(\theta_2, E_{\theta_1})}, y_{proj(\theta_2, J_{\theta_1})})$$

respectively. All voxels v of the intersection being considered therefore belong to the portion 21 of the volume of interest 20, as illustrated in FIG. 2.

If this condition is not fulfilled, we are in a situation similar to that illustrated in FIG. 3. Only a portion of the voxels v in the intersection being considered belong to the portion 21 of the volume of interest 20. Because of this, the intermediate three-dimensional mask M~ cannot be worked out for the entirety of the volume of interest 20, since information is missing as a result of the voxels v in the intersection being considered that are outside the portion 21 of the volume of interest 20 and that have not been "seen" by the means of recording 10 when the source is either at position $S_{\theta_2}$ or at a position $S_{\theta_1}$. There is therefore a column $1_{fin}$, outside of which it is not possible to work out the two-dimensional mask $M_{\theta_2}$. This column $1_{fin}$, fits a linear equation $$y = \max(y_{proj(\theta_2, E_{\theta_1})}, y_{proj(\theta_2, J_{\theta_1})})$$

and $$y = \min(y_{proj(\theta_2, E_{\theta_1})}, y_{proj(\theta_2, J_{\theta_1})})$$

respectively.

Then, for every column 1 of pixels contained between the last column d (or the first column d' respectively) and the column $1_{fin}$, whatever the voxel v belonging to the intersection of plane $P_1^{\theta_2}$ and the volume of interest 20, the intermediate three-dimensional mask M~ is determined by:

$$M\sim[v] = \begin{cases} 1 & \text{if } M\gamma[proj(\gamma v)] = 1 \\ 0 & \text{otherwise} \end{cases}$$

Then, in a third step, we project the three-dimensional mask M~ onto the column of pixels 1, making use of the position $S_{\theta_2}$ of the source S:

$$\forall \in \theta = \begin{cases} 1 & \text{if } \exists v \in \text{volume of interest (20) such that} \\ & proj(\theta_2, V)] = p \text{ and } M\sim(v) = 1 \\ 0 & \text{otherwise} \end{cases}$$

This allows the extrapolation of the two-dimensional mask $M_{\theta_2}$ onto pixel column 1 to be obtained.

Extrapolation for Two-Dimensional Masks $M_{\theta_2}$ Associated with Projections of the Extremity of the Source Trajectory S In this situation, the angle $\theta_2$ is equal to either $\theta_{max}$ or $\theta_{min}$. There is therefore no angle $\theta_1 > \theta_2 = \theta_{max}$ (or $\theta_1 < \theta_2 = \theta_{min}$ respectively) corresponding to a discrete position $S_{\theta_1}$ for the source close to position $S_{\theta_2}$ that would allow the procedure according to an embodiment of the invention to be used as described previously.

Figure 4:
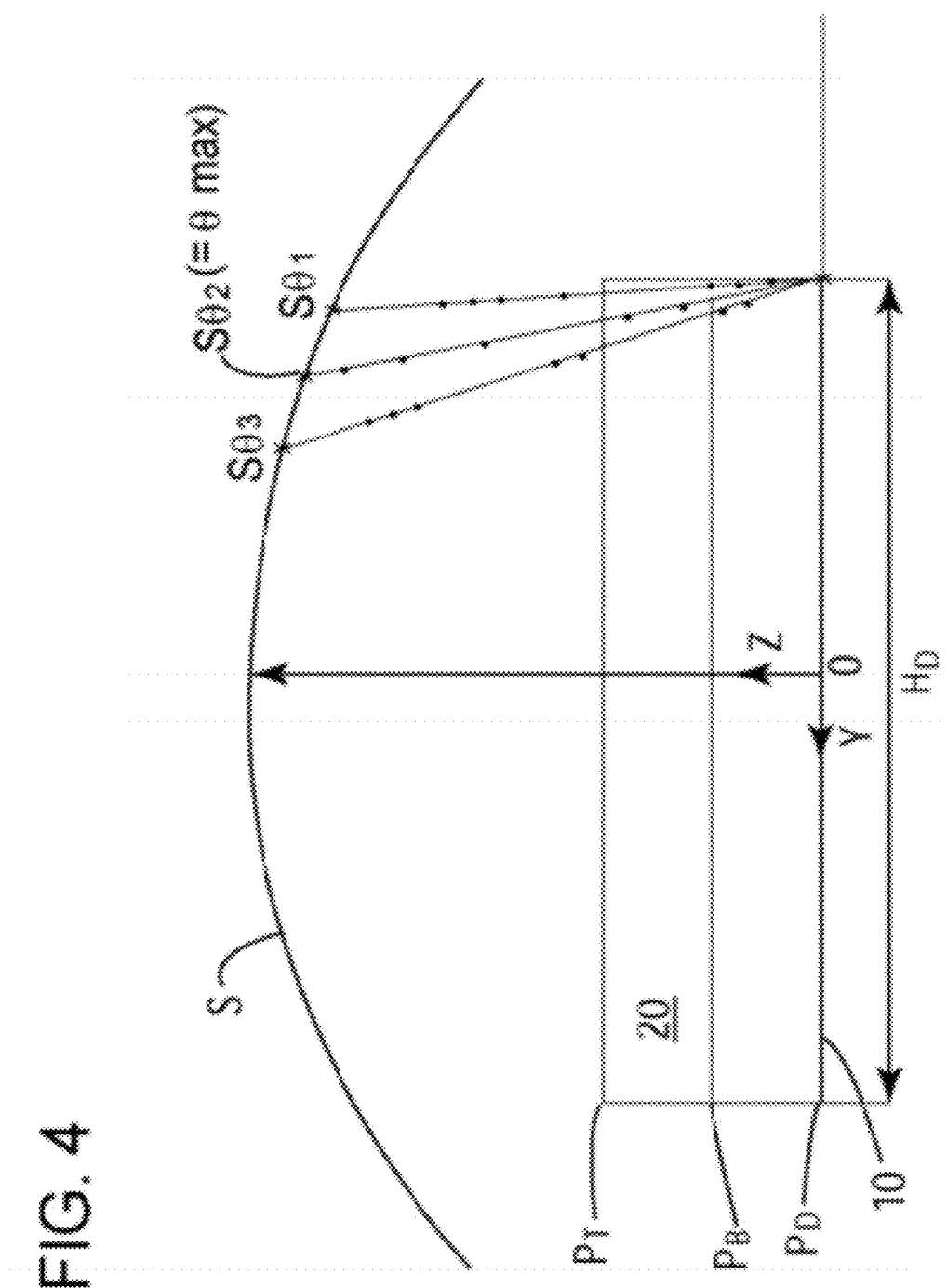
FIG. 4 is a schematic view from the side similar to FIGS. 2 and 3 illustrating the procedure in accordance with the invention for the extrapolation of a two-dimensional mask at the end of the series of two-dimensional masks to be extrapolated by the procedure in accordance with the invention.

To alleviate this situation and in order to apply the procedure as described according to the invention previously, we are going to extrapolate a position $S'_{\theta_1}$ for the source, associated with the angle $\theta_1 > \theta_2 = \theta_{max}$ (or $\theta_1 < \theta_2 = \theta_{min}$ respectively). To this end, let us take an angle $\theta_1 > \theta_2 =$ $\theta_{max\ (or\ \theta1)} < \theta_2 = \theta_{min}$ respectively) corresponding to a discrete source position $S_{\theta 3}$ close to position $S_{\theta 2}$ (see FIG. 4). We are therefore working out the position of point $T'_{\theta 1}$ on the final column d (or the first column d' respectively) making use of a linear interpolation between $T_{\theta 2}$ and $T_{\theta 3}$, as described previously for working out the point $T_\gamma$ starting from points $T_{\theta 1}$ and $T_{\theta 2}$. It is therefore sufficient to apply the procedure in accordance with the invention as described earlier.

Shapes of real objects likely to be present in the volume of interest 20:

To describe the procedure according to an embodiment of the invention, we have assumed the existence of a single point $T_\theta$ on the last column d (or the first column d' respectively). However, much of the time this is not the case: there are several points $T_\theta$ on this column d (or d' respectively). In order to resolve these cases, the procedure in accordance with the invention described previously is applied considering the points $T_\theta$ one at a time, giving an associated intermediate result. If there are three points $T_\theta$, for example, the procedure in accordance with the invention is applied three times and there are three associated intermediate results. Once all the points $T_\theta$ have been considered one after the other, the final result involves applying a logical AND to the entire group of associated intermediate results.

In one variant that can be realised, the logical AND is applied during the evaluation of the intersection between the volume of interest 20 and plane $P_1^{\theta 2}$.

Once all the two-dimensional masks have been extrapolated, the limit $l_{fin}$ is being removed by considering a virtual detector covering a zone that is common to all the extrapolated two-dimensional masks and by iterating the extrapolation procedure according to the invention as has just been described above.

Once the series of two-dimensional masks $M_{\theta 2}$ has been extrapolated this way, a final step can be applied to these masks in order to by sure that they are as natural as possible with respect to the object being X-rayed within the volume of interest 20. This final step is the application of a morphological closure based on a disc, with a diameter of a predetermined number of pixels. A morphological closure such as this consists of a dilation function based on the said disc followed by an erosion based on the same disc. This is a known method for image handling.

Determination of the Final Three-Dimensional Digital Mask:

Reconstruction of the final three-dimensional digital mask can then be realized based on the series of two-dimensional masks $M_{\theta 2}$ thus extrapolated. This type of reconstruction is well known. In order to avoid sudden transitions between the object and the background, a weighting (also known as "fuzzification") is always applied, making use of the theory of fuzzy sets.

To do this, member functions are associated with properties of the three-dimensional digital mask $M_{3d}$ ($M_{3d}[v]=1$ if the voxel v belongs to the object in question) and the two-dimensional mask $M_\theta$ ($M_\theta[p]=1$ if the pixel p belongs to the surface when the object in question is projected onto the plane $P_D$). Let these member functions be $\mu_{M3d}$ and $\mu_{M\theta}$ respectively. These member functions provide values that indicate how much the element complies with the property associated with the member function: these values range from 0 (the associated property is not the case) and 1 (the associated property is fully confirmed).

In order to determine the member function $\mu_{M\theta}$, the transition from 1 to 0 (object to background) is used that is present in the two-dimensional masks $M_\theta$ extrapolated as described earlier. In the current state of these two-dimensional masks, a precision error can arise at the transitions between object and background in the two-dimensional masks $M_\theta$. It is therefore sensible to balance or blur out the transition between the object and the background. To do this, the two-dimensional masks $M_\theta$ are treated as images in which the pixels take values from 0 (background) to 1 (object in question), to which a dilation based on a disc has been applied and then a low-pass filter. The dilation ensures that the kernel of the member function $\mu_{M\theta}$ (when this is equal to 1) covers the whole of the object under consideration, whereas applying a low-pass filter allows smooth transitions between the object and the background to be obtained. The size of the disc used for the dilation should correspond to the size of a kernel used when applying the low-pass filter (for example an average filter) once it has finished. This condition ensures that a result from applying the low-pass filter will be the same as the result in the zones of the two-dimensional mask $M_\theta$ "flagged" as belonging to the object under consideration, before the dilation.

As a variant, if the low-pass filter is an infinite impulse response filter (such as a Gaussian filter), the size of the dilation disc should be a value based on which the coefficients of the kernel of the low-pass filter can be disregarded (in a Gaussian filter, the kernel can be small if the deviation type is small and if the coefficients are only represented by a few of the bits, in IT terms).

It should be noted that the precision error can be modelled by the size of the kernel of the low-pass filter: filters with large kernels containing significant values rarely retain the low frequencies and therefore smear out (make fuzzy, balance out) the transitions between the object and the background more.

Figure 5:
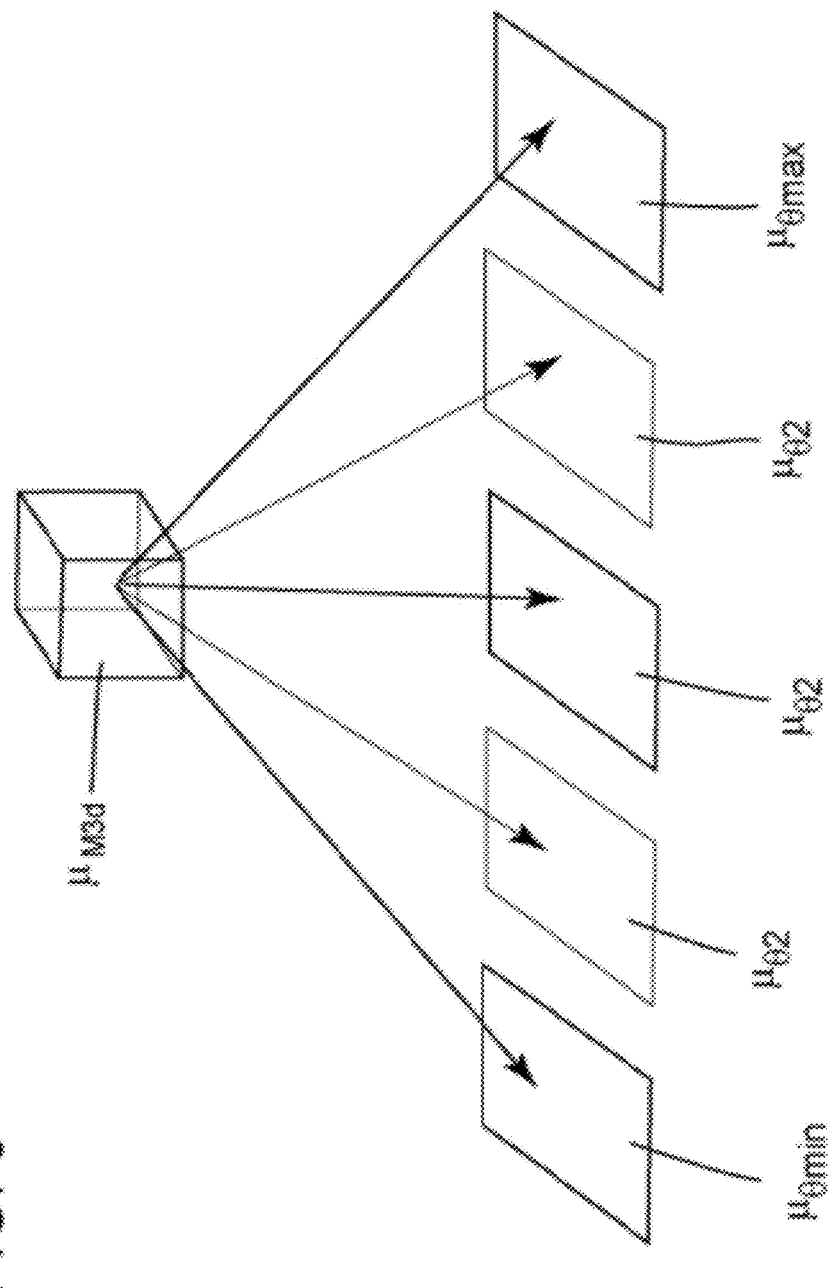
FIG. 5 is a schematic view of a step for determining a three-dimensional digital mask by the procedure in accordance with the invention.

In order to determine the member function $\mu_{M3d}$ corresponding to the property associated with the three-dimensional digital mask $M_{3d}$, the information supplied by the properties associated with the two-dimensional masks $M_\theta$ (for each angle θ associated with each two-dimensional mask in the series of extrapolated two-dimensional masks) must be reassembled making use of an aggregation operator (see FIG. 5). An aggregation operator such as this could be a t-norm operator T. This allows the member function $\mu_{M3d}$ to be calculated as a fuzzy counterpart of the logical AND. Numerous t-norm operators exist: probabilistic, drastic, Zadeh, Lukasiewicz, etc. The procedure has been implemented using the probabilistic t-norm operator.

The member function $\mu_{M3d}$ is therefore determined as follows: $\forall v \in$ volume of interest (20), $$\mu_{M_{3d}}(v) = T_\theta \mu_{M_\theta}(proj(\theta, v))$$

We thus obtain a final weighted three-dimensional digital mask $M_{3d}$.

There are of course numerous modifications that can be applied to various embodiments of the invention such as that described above without deviating from the framework described for it.

In this document, the terms "procedure" and "method" are used interchangeably.

This written description uses examples to disclose embodiments of the invention, including the best mode, and also to enable any person skilled in the art to make and use the claimed invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Although specific features of embodiments of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the scope of the following claims.

The invention claimed is:

1. A computer-implemented method for processing radiographic images by extrapolating a two-dimensional mask $M_{\theta 2}$ from a series of two-dimensional masks, the method comprising:
   at a radiographic device comprising an X-ray source and a digital detector that is in planar arrangement opposite the source and which has a limit (d, d'):
   a) recording a series of images at a series of positions $S_\gamma$ for the X-ray source of a volume of interest consisting of an object located between the X-ray source and the digital detector;
   b) calculating a series of two-dimensional masks $M_\gamma$ from the series of images, the series of two-dimensional masks $M_\gamma$ associated with the series of positions $S_\gamma$ for the X-ray source, located between a first position $S_{\theta 1}$ and a second position $S_{\theta 2}$ for the X-ray source, starting from a first two-dimensional mask $M_{\theta 1}$ and a second two-dimensional mask $M_{\theta 2}$;
   c) calculating an intermediate three-dimensional mask for the object, starting from the series of two-dimensional masks $M_\theta$ and the first two-dimensional mask $M_{\theta 1}$ and the second two-dimensional mask $M_{\theta 2}$;
   d) extrapolating the second two-dimensional mask $M_{\theta 2}$ beyond the limits d or d' of the digital detector, according to a relative position between the first position $S_{\theta 1}$ and the second position $S_{\theta 2}$, starting from the intermediate three-dimensional mask; and
   e) reconstructing a final three-dimensional digital mask from a resulting series of extrapolated two-dimensional masks $M_{\theta 2}$.

2. The computer-implemented method of claim 1, wherein before step b), if the first two-dimensional mask $M_{\theta 1}$ associated with the first position $S_{\theta 1}$ is not available, the method further includes a step for extrapolating the first two-dimensional mask $M_{\theta 1}$ from the available two-dimensional masks $M_\theta$.

3. The computer-implemented method of claim 1, further comprising projecting the intermediate three-dimensional mask based on the second position $S_{\theta 2}$ onto a plane passing through the digital detector.

4. The computer-implemented method of claim 1, wherein the at least partially estimating step b) is carried out at the limit d or d' of the digital detector, according to the relative position between the first position $S_{\theta 1}$ and the second position $S_{\theta 2}$.

5. The computer-implemented extrapolation method of claim 4, wherein for each of the two-dimensional masks $M_\gamma$, the at least partially estimation from step b) involves a step that determines a point $T_\gamma$ situated at an edge of the object, projected onto the limit d or d' of the digital recorder, with the source at position $S_\gamma$.

6. The method of claim 5, wherein the point $T_\theta$ are estimated by linear interpolation between a first point $T_{\theta 1}$ and a second point $T_{\theta 2}$ located at an edge of the object projected onto the limit d or d' of the digital detector, with the source at the first position $S_{\theta 1}$ and the second position $S_{\theta 2}$ respectively.

7. The computer-implemented extrapolation method of claim 6, wherein if the first two-dimensional mask $M_{\theta 1}$ associated with first position $S_{\theta 1}$ is not available, the method includes extrapolating the first point $T_{\theta 1}$ from the points $T_\theta$ that are available.

8. The computer-implemented method of claim 1, further comprising applying a closure function to the extrapolated second two-dimensional mask $M_{\theta 2}$.

9. The extrapolation method of claim 1, wherein before step b), the method further comprises a step for determining a limit of extrapolation $l_{fin}$ that is effectively parallel to the limit d or d' of the digital detector and that is located outside the limits of the digital detector.

10. The computer-implemented method of claim 9, wherein for every line l that is that is effectively parallel to the limit of extrapolation $l_{fin}$ and located between the limit d or d' of the digital detector and the limit of extrapolation $l_{fin}$, the step c) further comprises the following steps:
    working out a plane $P_1^{\theta 2}$ that passes through the second position $S_{\theta 2}$ and the line l; and
    working out an intermediate three-dimensional mask for each voxel (v) located at the intersection of the plane $P_1^{\theta 2}$ and the volume of interest.

11. The computer-implemented method of claim 10, wherein the step further comprises a projection step for every line l that is effectively parallel to the limit of extrapolation $l_{fin}$ and located between the limit d or d' of the digital detector and the limit of extrapolation $l_{fin}$ for the intermediate three-dimensional mask.

12. A computer-implemented method for processing images radiographic images by calculating a three-dimensional mask based on a series of two-dimensional masks $M_\theta$, the method consisting of the following steps:
    at a radiographic device comprising an X-ray source and a digital detector that is in planar arrangement opposite the source and which has a limit (d, d'):
    a) recording a series of images at a series of positions $S_\gamma$ for the X-ray source of a volume of interest consisting of an object located between the X-ray source and the digital detector;
    b) extrapolating the a series of two-dimensional masks $M_\gamma$ by:
       b1) estimating a series of two-dimensional masks $M_\gamma$ associated with a series of positions $S_\theta$ for the X-ray source, located between a first position $S_{\theta 1}$ and a second position $S_{\theta 2}$ of the X-ray source, starting from a first two-dimensional mask $M_{\theta 1}$ and a second two-dimensional mask $M_{\theta 2}$;
       b2) evaluating an intermediate three-dimensional mask for the object, starting from the series of two-dimensional masks $M_\gamma$ and the first two-dimensional mask $M_{\theta 1}$ and the second two-dimensional mask $M_{\theta 2}$; and
       b3) extrapolating the second two-dimensional mask $M_{\theta 2}$ beyond the limits d or d' of the digital detector, according to a relative position between the first position $S_{\theta 1}$ and the second position $S_{\theta 2}$, starting from the intermediate three-dimensional mask; and
    c) reconstructing a three-dimensional digital mask based on the extrapolated series of two-dimensional masks $M_\theta$.

13. The computer-implemented method of claim 12, wherein step c) includes steps involving:

c1) applying a dilation function followed by a low-pass filter to obtain a membership function $\mu_{M\theta}$ for each two-dimensional mask $M_\theta$;
c2) evaluating a membership function $\mu_{M3d}$ based on the membership function $\mu_{M\theta}$, using a T-norm operator; and
c3) determining the three-dimensional digital mask based on the membership function $\mu_{M3d}$.

14. The computer-implemented method of claim 13, wherein the t-norm operator is probabilistic.

* * * * *

UNITED STATES PATENT AND TRADEMARK OFFICE
CERTIFICATE OF CORRECTION

PATENT NO. : 8,335,809 B2  
APPLICATION NO. : 12/339209  
DATED : December 18, 2012  
INVENTOR(S) : Palma et al.

Page 1 of 2

It is certified that error appears in the above-identified patent and that said Letters Patent is hereby corrected as shown below:

On the Title Page, in Item (57), under "ABSTRACT", in Column 2, Line 4, delete "hat" and insert -- that --, therefor.

On the Title Page, in Item (57), under "ABSTRACT", in Column 2, Line 7, delete "$1_{fin}$" and insert -- $l_{fin}$ --, therefor.

On the Title Page, in Item (57), under "ABSTRACT", in Column 2, Line 12, delete "$1_{fin}$," and insert -- $l_{fin}$ --, therefor.

On the Title Page, in Item (57), under "ABSTRACT", in Column 2, Line 13, delete "mask (21)" and insert -- mask --, therefor.

In the Specifications:

In Column 2, Line 61, delete "$M_{\theta 2}$" and insert -- $M_{\theta 2}$; --, therefor.

In Column 2, Line 65, delete "$M_{\theta 2}$" and insert -- $M_{\theta 2}$; --, therefor.

In Column 3, Line 2, delete "mask" and insert -- mask. --, therefor.

In Column 3, Line 15, delete "$_{\theta 1}$" and insert -- $S_{\theta 1}$ --, therefor.

In Column 3, Line 20, delete "$S\gamma$" and insert -- $S\gamma$; --, therefor.

In Column 3, Line 33, delete "$l_{fin}$," and insert -- $l_{fin}$ --, therefor.

In Column 3, Line 46, delete "$l_{fin}$," and insert -- $l_{fin}$ --, therefor.

In Column 3, Line 48, delete "$l_{fin}$," and insert -- $l_{fin}$ --, therefor.

Signed and Sealed this  
Thirtieth Day of April, 2013

Teresa Stanek Rea  
*Acting Director of the United States Patent and Trademark Office*

CERTIFICATE OF CORRECTION (continued)
U.S. Pat. No. 8,335,809 B2

In Column 3, Lines 49-55, delete "[0011] In accordance with the invention,..........earlier." and insert -- In accordance with the invention,..........earlier. --, therefor at Line 50, as a new paragraph.

In Column 6, Lines 21-24, delete "[0029] $\forall \theta \in [0;\pi]$,..............$z_{s\theta} \leq r \sin(\theta)+z_c$." and insert -- $\forall \theta \in [0;\pi]$, $S_\theta$ is the position of the source on the trajectory of angle $\theta$ with respect to the y-axis. Therefore $\forall \theta \in [0;\pi]$, $x_{s\theta}=0$; $y_{s\theta}=r \cos(\theta)$, $z_{s\theta}=r \sin(\theta)+z_c$. --, therefor.

In Column 6, Line 59, delete "$S\theta_2$" and insert -- $S_{\theta 2}$ --, therefor.

In Column 6, Line 64, delete "$S\theta_2$." and insert -- $S_{\theta 2}$. --, therefor.

In Column 8, Line 14, delete "$1_{fin}$," and insert -- $l_{fin}$ --, therefor.

In Column 8, Line 16, delete "$1_{fin}$," and insert -- $l_{fin}$ --, therefor.

In Column 8, Line 31, delete "$1_{fin}$," and insert -- $l_{fin}$, --, therefor.

In Columns 8 & 9, Lines 67 & 1, delete "$\theta_1 > \theta_2 = \theta max_{(or\,\theta 1} < \theta 2 = \theta_{min}$" and insert -- $\theta_2 > \theta_3$(or $\theta_2 < \theta_3$ --, therefor.

In Column 9, Line 29, delete "$l_{fin}$," and insert -- $l_{fin}$ --, therefor.

In Column 9, Line 36, delete "by" and insert -- be --, therefor.

In the Claims:

In Column 11, Line 37, in Claim 1, delete "$M_\theta$" and insert -- $M_\gamma$ --, therefor.

In Column 11, Line 62, in Claim 5, delete "extrapolation method" and insert -- method --, therefor.

In Column 12, Line 1, in Claim 6, delete "$T_\theta$are" and insert -- $T_\gamma$ are --, therefor.

In Column 12, Line 6, in Claim 7, delete "extrapolation method" and insert -- method --, therefor.

In Column 12, Line 14, in Claim 9, delete "extrapolation method" and insert -- method --, therefor.

In Column 12, Line 20, in Claim 10, delete "that is that is" and insert -- that is --, therefor.

In Column 12, Line 49, in Claim 12, delete "$S_\theta$" and insert -- $S_\gamma$ --, therefor.